US012087450B2

(12) United States Patent
Stirling

(10) Patent No.: US 12,087,450 B2
(45) Date of Patent: Sep. 10, 2024

(54) APPARATUS AND METHOD FOR DETECTION AND MITIGATION OF CONDITIONS THAT ARE FAVORABLE FOR TRANSMISSION OF RESPIRATORY DISEASES

(71) Applicant: Robert E. Stirling, Abbotsford (CA)

(72) Inventor: Robert E. Stirling, Abbotsford (CA)

(73) Assignee: Robert E. Stirling, Abbotsford (CA)

( * ) Notice: Subject to any disclaimer, the term of this patent is extended or adjusted under 35 U.S.C. 154(b) by 0 days.

(21) Appl. No.: 17/473,800

(22) Filed: Sep. 13, 2021

(65) Prior Publication Data

US 2023/0223154 A1 Jul. 13, 2023

(51) Int. Cl.
*G16H 50/80* (2018.01)
*G01N 25/66* (2006.01)
*G08B 21/18* (2006.01)

(52) U.S. Cl.
CPC ............ *G16H 50/80* (2018.01); *G01N 25/66* (2013.01); *G08B 21/182* (2013.01)

(58) Field of Classification Search
CPC ........ G16H 50/80; G16H 50/70; G16H 40/63; G01N 25/66; G08B 21/182
USPC ......................................................... 340/602
See application file for complete search history.

(56) References Cited

U.S. PATENT DOCUMENTS

| | | | |
|---|---|---|---|
| 8,085,145 B2 | 12/2011 | Fu et al. | |
| 2009/0112114 A1 | 4/2009 | Ayyagari et al. | |
| 2015/0077737 A1* | 3/2015 | Belinsky | G01N 15/0211 250/208.2 |
| 2019/0080801 A1 | 3/2019 | Klos et al. | |
| 2021/0236003 A1 | 8/2021 | LeBoeuf et al. | |
| 2021/0345069 A1 | 11/2021 | Hunter | |
| 2022/0136730 A1* | 5/2022 | Schoch | G08B 21/12 700/276 |
| 2022/0246304 A1 | 8/2022 | Shyu et al. | |
| 2022/0275966 A1 | 9/2022 | Schoch et al. | |

FOREIGN PATENT DOCUMENTS

| | | | |
|---|---|---|---|
| KR | 20210025927 A | * | 3/2021 |
| KR | 20210069463 A | * | 6/2021 |
| WO | 2017216056 A1 | | 12/2017 |

OTHER PUBLICATIONS

Anderson et al., "Dry-air and hyperosmolar challenge in asthma and rhinitis," *Asthma and Rhinitis* 2:1449-1468, 1995. (21 pages).

(Continued)

*Primary Examiner* — Eric Blount
(74) *Attorney, Agent, or Firm* — Seed IP Law Group LLP

(57) ABSTRACT

Systems and methods are provided for detecting a potential for dewpoint respiratory inoculation (DRI). A method includes detecting a change in temperature over time, determining a slope of the change in temperature, comparing the slope of change in temperature with a slope threshold, and if the slope of change in temperature exceeds the slope threshold, then signaling a potential for dewpoint respiratory inoculation. Detection systems can include a personal device with temperature and humidity detectors, a processor for collecting data and identifying conditions that may provoke DRI, and providing a signal to the user.

20 Claims, 4 Drawing Sheets

(56) References Cited

OTHER PUBLICATIONS

Figure 1A:
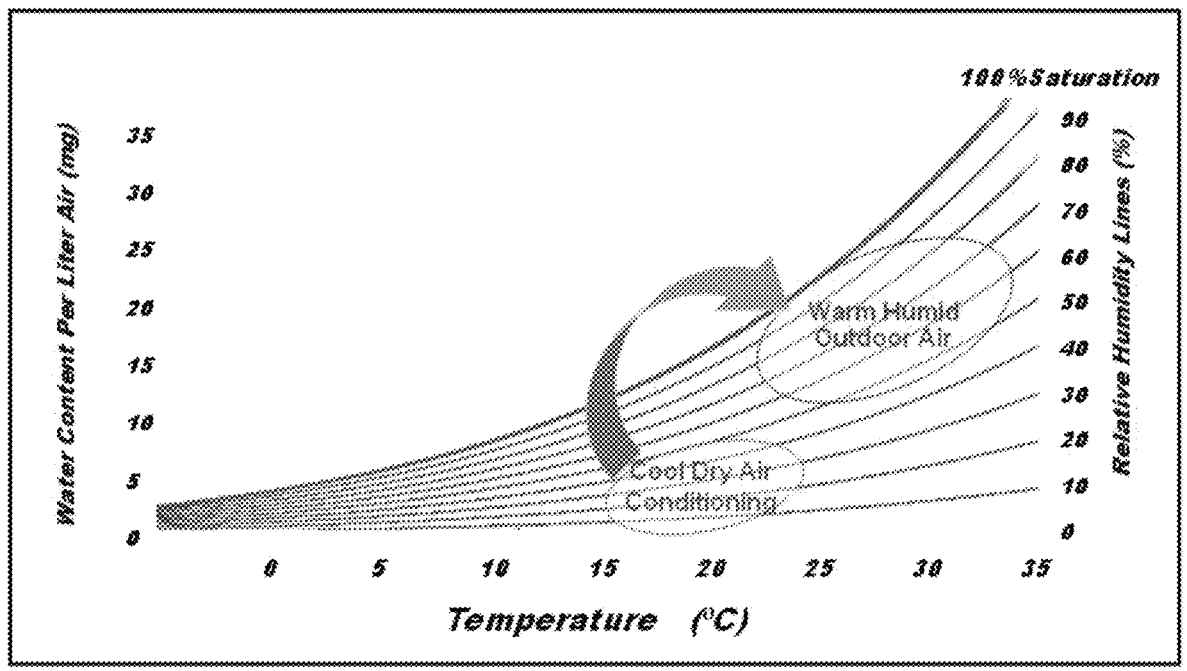

Anonymous, "Chapters 13-24: College Physics—Textbook Equity Edition," *Openstax College* 2:431-470, 2013. (48 pages).
Banerjee et al., "Novel Insights Into Immune Systems of Bats," *Frontiers in Immunology* 11:1-15, Jan. 2020. (15 pages).
Cole et al., "Effects of Cold Air and Exercise on Nasal Patency," *Ann Otol Rhinol Laryngol* 92:196-198, 1983. (3 pages).
Jacobs et al., "Human Rhinoviruses," *Clinical Microbiology Reviews* 26(1): 135-162, Jan. 2013. (28 pages).
Koskela et al., "Cold air-provoked respiratory symptoms: the mechanisms and management," *International Journal of Circumpolar Health* 66(2):135-162, Apr. 1, 2007. (11 pages).
Linden et al., "Mucins in the mucosal barrier to infection," *Mucosal Immunology* 1(3):183-197, May 2008. (15 pages).
Parrish et al., "Cross-Species Virus Transmission and the Emergence of New Epidemic Diseases," *Microbiology and Molecular Biology Reviews* 72(3):457-470, Sep. 2008. (14 pages).
Read et al., "The Role of Zinc in Antiviral Immunity," *American Society for Nutrition* 10:696-710, 2019. (15 pages).
Stirling, "A Discussion of Behavioral Causality Between Humanity and Pandemics," *Not a 'Cold', but a D.R.I.* 1.2:1-7, Jul. 12, 2020. (7 pages).
Wakabayashi et al., "Lactoferrin for prevention of common viral infections," *Journal of Infection and Chemotherapy* 20:666-671, Aug. 30, 2014. (6 pages).
Woolhouse et al., "Ecological Origins of Novel Human Pathogens," *Critical Reviews in Microbiology* 33:231-242, Aug. 24, 2007. (13 pages).
World Health Organization, "Infection of farmed animals with the pandemic virus," 2009, URL=https://web.archive.org/web/20091109052428/http://www.who.int/csr/disease/swineflu/notes/briefing_20091105/en/print.html, retrieved on Mar. 27, 2024. (2 pages).
Zanin et al., "The Interaction between Respiratory Pathogens and Mucus," *Cell Host & Microbe* 19:159-168, Feb. 10, 2016. (10 pages).
Zhong et al., "The immunology of COVID-19: is immune modulation an option for treatment?," *Lancet Rheumatol* 2:e428-36, May 20, 2020. (10 pages).

\* cited by examiner

APPARATUS AND METHOD FOR DETECTION AND MITIGATION OF CONDITIONS THAT ARE FAVORABLE FOR TRANSMISSION OF RESPIRATORY DISEASES

RELATED CASES

This application claims the benefit of Provisional Patent Application Ser. No. 63/050,875, filed Jul. 13, 2020.

BACKGROUND

Field of the Invention

The present disclosure relates generally to systems and processes for detecting transient conditions of increased danger of respiratory disease infection, and more particularly, to detection of conditions in which the likelihood of condensation of water from ambient air onto the linings of a subject's airways is increased.

Related Art

The human body has a very effective, tiered system for preventing harm due infection, parasites, harmful chemicals, environmental factors, etc., and for regulating normal body function under varying environmental conditions. For example, the immune system is a cell-mediated system that works to combat and eliminate pathogens that may have entered the body, to prevent or minimize damage that might otherwise occur. However, there are a number of processes, structures, and elements that work to prevent the entry of these harmful substances and pathogens into the body in the first place. Included in this group are various mucous membranes—mucosa—including membranes that line the nasal passages, sinuses, mouth, throat, trachea, and bronchioles of the lungs, which secrete a layer of mucous. This mucous traps foreign matter, such as pathogens, pollen, dust, etc., which would otherwise be inhaled into the lungs, while acting as a barrier, to preventing pathogens, in particular, from contacting the mucosa directly Mucous also has antiseptic/antimicrobial properties to combat pathogens in the airways. Additionally, inhaled air is warmed and humidified by contact with mucous, so that, ideally, by the time it reaches the lungs it has been warmed to within a few degrees of normal body temperature and is near 100% relative humidity.

When the condition of the air changes, the body responds by modifying the production of mucous in order to maintain a constant supply of clean, warm, and humid air. For example, if the ambient temperature drops, the body's production of mucous will increase. This serves two purposes: First, colder air requires more thermal energy to bring it to body temperature than warm air, and the larger volume of mucous carries more thermal energy into the nasal passages to accomplish this. And second, as air temperature increases, its relative humidity drops, and it becomes drier. The increase in mucous production provides additional moisture to properly humidify the air.

BRIEF DESCRIPTION OF THE DRAWINGS

FIGS. 1A and 1B are charts showing the water content per liter of air at various temperatures, and the corresponding relative humidity at those temperatures.

FIG. 2 is a block diagram of a Dewpoint Respiratory Inoculation (DRI) detector, according to an embodiment, which is configured to be carried by a user, to monitor the ambient environment, and to warn the user when conditions may provoke DRI.

FIG. 3 is a flow chart showing a process for detecting conditions that have the potential of provoking DRI, according to an embodiment.

FIG. 4 is a diagrammatic side view showing an example of a system for protecting individuals from DRI as they enter and exit a building, according to an embodiment.

DETAILED DESCRIPTION

There is a well-recognized statistical relationship between seasonal changes in temperature and humidity and the incidence of respiratory illnesses, such as, e.g., influenza and coronaviruses. The particular mechanism(s) responsible for the correlation are not well understood. In particular, there appears to be a stronger correlation between conditions in which individuals are subjected to artificially controlled environments and the incidence of infections than those in which the variations in temperature and humidity occur naturally. In other words, people who work primarily outdoors and/or live and work in environments that are not strongly temperature regulated year around are statistically less susceptible to various kinds of infections than people who live and/or work in spaces that are highly regulated by HVAC systems. This is puzzling because, on the one hand, there is a recognized correlation between seasonal variations and the incidence of respiratory infections, while on the other hand, those people who are the least exposed to such variations, i.e., those who spend much of their time in climate-controlled conditions, appear to be the most susceptible to infection.

Many theories have been proposed to explain these and related issues, but the available answers have so far not been fully satisfactory. The inventor believes that the significance of these correlations has not been fully understood by previous theorists, and that a significant contributing factor to these phenomena is Dewpoint Respiratory Inoculation (DRI), as explained below.

It is widely understood that airborne pathogens are frequently carried on small water droplets that are exhaled by contagious individuals. In a dry environment, the droplets quickly evaporate and become gaseous, so that the pathogens—and other vapor-borne contaminants—are no longer supported and fall out of the air. However, in a relatively humid environment water droplets can be quite persistent, the smallest of which can remain in the air for many minutes after being exhaled by a contagious individual. One of the functions of mucous in the airway is to capture these droplets, which can be transported away from the lungs by processes such as ciliary action, then removed from the airway via coughing, sneezing, swallowing, etc.

As noted above, the human body is able to regulate the production of mucous in response to changes in temperature and humidity. However, the inventor has recognized that such regulation is not unlimited in capacity, nor is it instantaneous. First, even though the rate of mucous production is variable, an individual's airway can become generally drier in very dry conditions. Second, as the individual inhales and exhales, the conditions in the airway fluctuate in response to the air passing through. When cold, dry air is inhaled, the air does not become instantly warm and humid, but instead is progressively conditioned along the length of the airway, and will dry and chill the mucous and membranes in the nasal passages as it becomes warmer and more humid.

The process is reversed as the individual exhales warm, moist air across the depleted membranes, so that the drying and chilling effect is repeated with each breath. This will occur, in particular, in those portions of the nasal passages first encountered as the air enters the passages, but can extend the length of the airway and even into the lungs, depending upon the ambient conditions and volume of the inflowing air (a person who is breathing hard will inhale and exhale a higher volume of air per unit of time). Under more extreme conditions, a greater length of the airway will be chilled and dried by the air. If the air is relatively cold, this will occur regardless of the relative humidity of the air, because as even very humid cold air is warmed, its relative humidity plummets, and it becomes relatively very dry. However, even warm air can produce the same effect if it is very dry: rapid evaporation of moisture in the mucous, as will happen if the air is extremely dry, will cause the temperature of the mucous and mucosa to drop. This drying and chilling effect leaves the mucosa less protected from pathogens in the air. Drying and thickening of the mucous can inhibit mucociliary function, and pathogens that settle on depleted (partially dehydrated) mucous or directly on an exposed surface of a mucous membrane are less likely to be encapsulated by mucous that is formed thereafter, but may instead establish a colony, so that the individual becomes infected by the pathogen.

Figure 1B:
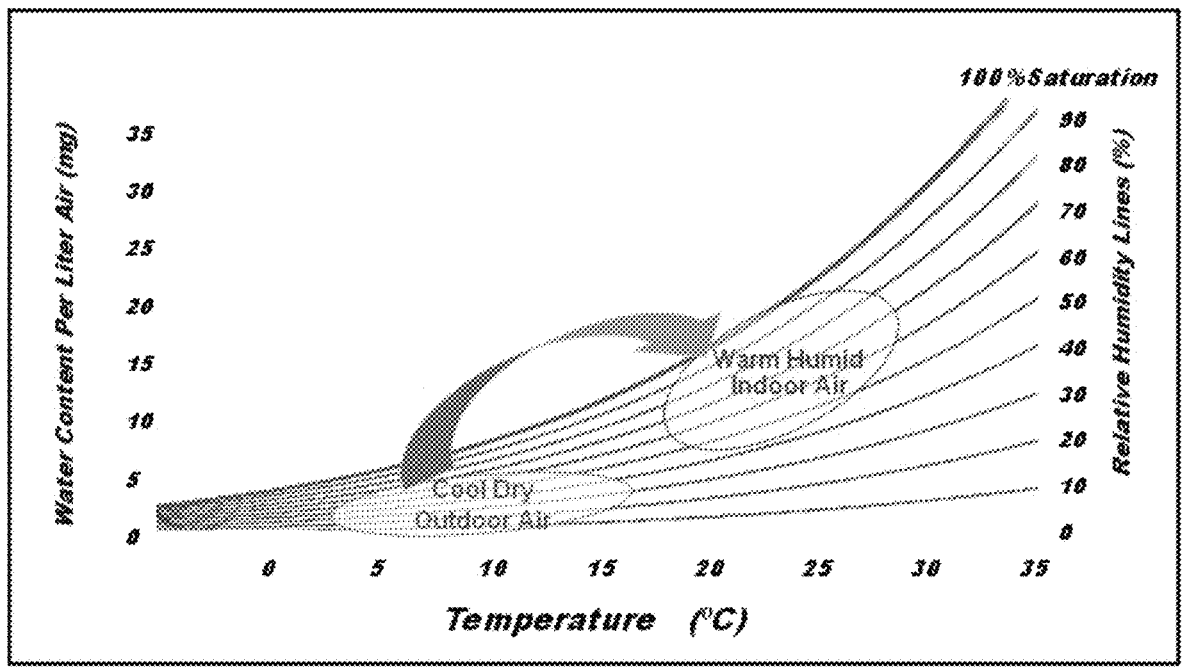

FIGS. 1A and 1B are charts showing the water content per liter of air at various temperatures, and the corresponding relative humidity at those temperatures. The dew point corresponds to the 100% humidity line. If air that is fully saturated—i.e., at 100% humidity—drops in temperature, sufficient water will precipitate from the air onto nearby surfaces so that the relative humidity stays at or below 100% relative humidity. Thus, if the outside temperature is 32° C. (about 90° F.) with 80% humidity, the air will reach saturation—i.e., 100% relative humidity—if cooled to around 28° C. (about 82° F.), and further cooling will cause water to precipitate. If this occurs in nasal passages that have been dried and chilled by a period of exposure to cool or cold, dry air, and if the first moisture that reaches the surfaces of those passages is laden with pathogens, the individual risks inoculation by one or another of the pathogens. Hence, Dewpoint Respiratory Inoculation.

The inventor has recognized that this vulnerability is most acute in the moments after an individual passes into a humid environment but before the mucosa in the nasal passages recovers from the previously dry conditions. If the ambient air changes very quickly from cold and dry to warm and humid, warm air entering the nasal passages will actually be initially chilled, as it enters the nasal passages, by contact with the surfaces that had been previously cooled by the colder environment. This chilling can cause the incoming humid air to drop below its dew point temperature, so that humidity from the air precipitates to water on the surfaces of the nasal passages before mucous can be reformed. This can happen, for example, when an individual leaves an airconditioned building on a hot, humid, summer day, as shown by the arrow in FIG. 1A, or when the individual enters a heated building on a cold winter day as shown by the arrow in FIG. 1B. The mucous membranes are momentarily moistened by precipitating water vapor rather than mucous, so that pathogens deposited there by microdroplets in the air may find an ideal surface for establishing a colony.

Thus, the inventor believes that the point of greatest danger of infection occurs in what might be referred to as a critical transition zone (CTZ) that can be present between an artificially controlled environment and the surrounding natural environment, in which the differences in temperature and humidity are sufficient to provoke DRI, as an individual moves from a cool or cold environment to a warm or hot environment, particularly when humidity in the warmer environment is relatively high.

The period during which the body is most vulnerable as it adjusts to the new environment may be only a few seconds or may last longer, depending upon factors such as the magnitude of the transition in temperature, the humidity of the warmer environment, and the length of time spent by the individual in the colder environment, during which the individual's nasal passages may become progressively drier. Individuals who spend most of their time in climate-controlled environments may cross through many CTZs over the course of a day, as they transition from home to vehicle to work, etc. At each transition, these individuals are subjected to a short period during which their natural defenses may be compromised.

This is in contrast to situations in which individuals may live in homes that are not airconditioned, and/or work outdoors or in facilities that are not airconditioned. In these circumstances, the transitions are usually fewer, less abrupt, and of lower magnitudes, producing conditions that are less likely to provoke DRI.

The inventor also believes that drinking a cold beverage in a warm and humid environment can also provoke DRI, as the cold liquid chills the throat and nasal passages, after which warm air inhaled by the individual may be chilled to its dewpoint in the individual's throat or nasal passages.

The inventor is not aware of any previous work evaluating the effect, specifically, of these transition zones on the susceptibility of an individual to airborne pathogens. The inventor proposes a number of systems and processes that address this problem in various ways, according to respective embodiments.

A first step in protecting an individual from DRI is notification. If a person is aware of the possibility of DRI in a particular situation, she may be able to take measures to mitigate the danger of infection. Therefore, according to an embodiment, a device is provided that is configured to detect abrupt changes in temperature and humidity, and warn the user of a temperature change of sufficient amplitude and sufficiently short duration as to potentially provoke DRI. Embodiments are also contemplated that provide various responses to conditions in which DRI is a potential problem.

FIG. 2 is a block diagram of a DRI detector 100 that is carried by a user and configured to monitor the ambient environment, and to warn the user when conditions may provoke DRI, according to an embodiment. The detector 100 includes a case 102 that can be worn outside the user's clothing on a cord or chain, or that can be clipped to the user's clothing—but away from where it might be influenced by the user's own breath. Mounted to the case 102 are a temperature sensor 104, a humidity sensor 106, a signal lamp 108 and a signal speaker 110. Within the case, a signal conditioning module 112 is configured to receive signals from the temperature and humidity sensors 104, 106, and to output a conditioned signal for each to a logic module 114. A clock 116 is also configured to provide a timing signal to the logic module 114, and a memory 118 is configured to store data and timing information used by the logic module. An alarm module 120 is configured to provide alerts to the user, and a wireless transceiver module 122, such as, e.g., a Bluetooth module, is configured to communicate with another device, such as a user's smartphone, etc. A battery 124 is configured to provide power to each of the components of the DRI detector 100. The logic module 114 is configured to receive the conditioned signals from the signal conditioning module 112 and the timing signal from the clock 116, and, on the basis of changes in the values of the conditioned signals over time, detect conditions that could provoke DRI. The alarm module 120 is configured to receive an alarm command from the logic circuit 114 and to provide a visual and/or audible alarm signal via the signal lamp 108 or the signal speaker, or via the wireless module 122, depending upon preference settings and configuration of the device.

Figure 2:
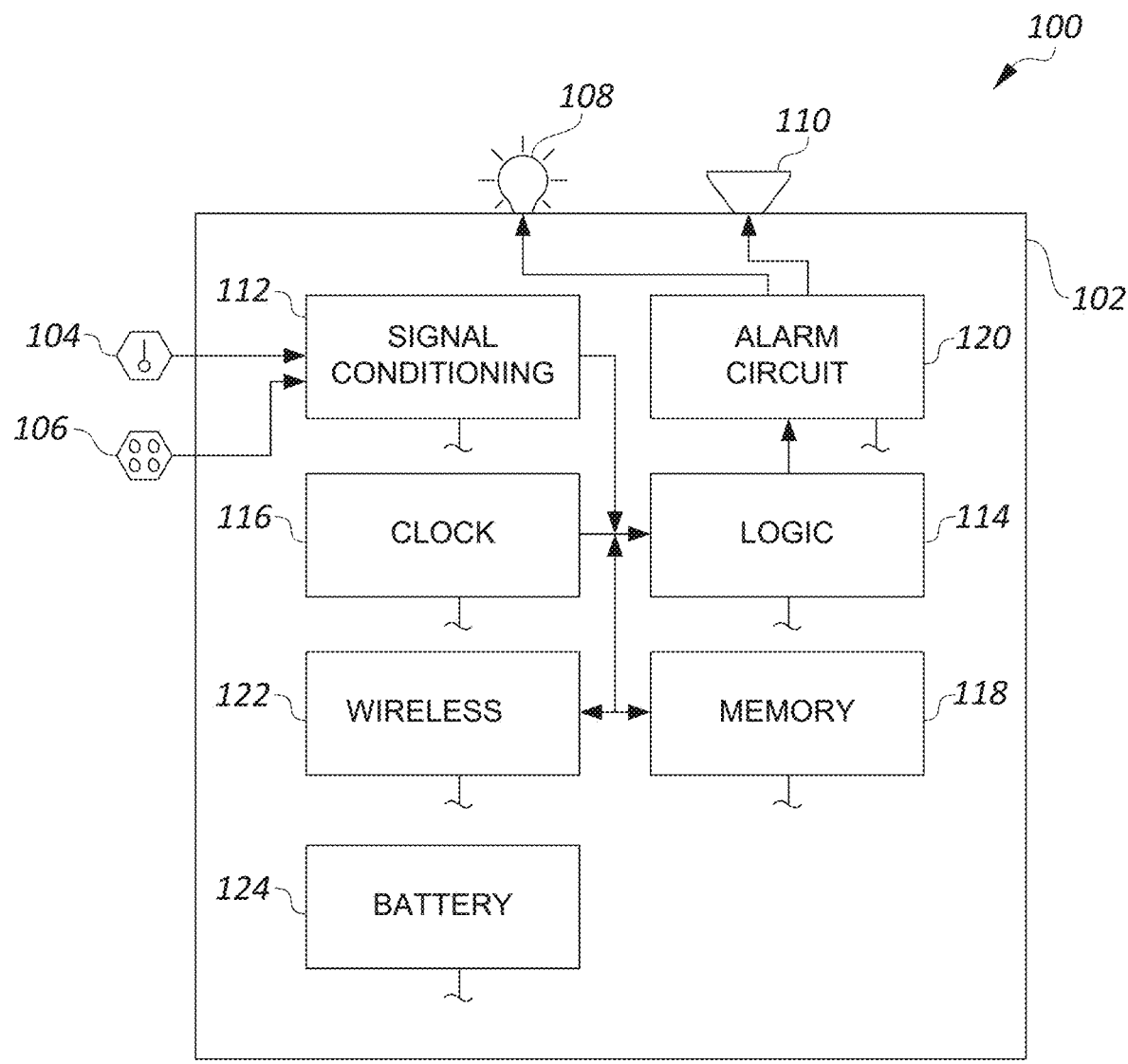

According to one embodiment, the system shown in FIG. 2 employs a digital circuit. According to another embodiment, an analogue circuit is used, which, may include, for example, an integrator circuit to detect the slope of the incoming temperature signal, the charge constant of a capacitor and resistor to define the slope threshold, and a comparator to detect conditions that exceed the threshold.

Various embodiments are envisioned that include different combinations of the elements shown and described with reference to FIG. 2. For example, according to one embodiment, the wireless module 122 is omitted, and all functions are performed by components within the case 102. In another embodiment, the humidity sensor 104 is omitted, and the device is configured to detect a potential DRI based on temperature changes, alone.

According to a further embodiment, a separate device is provided, e.g., a smartphone or other personal digital device, which is configured to perform the functions of many of the modules shown in FIG. 2, such as the logic module 114, the memory 118, and the signal module 120, as well as the signal output components, i.e., the signal lamp 108 and the signal speaker 110. Accordingly, these elements are omitted as physical components within the case 102 of the DRI detector 100. In this embodiment, the components within the case 102 provide sensor functions while the separate device provides processor functions.

In the description of the embodiment of FIG. 2, various components and modules are described as separate elements, for clarity of description. However, in other embodiments these elements are combined into fewer elements or separated into more elements that nevertheless perform the defined functions. Furthermore, in some embodiments elements are distributed among multiple devices that cooperate to perform the necessary functions. Furthermore, those multiple device may also be configured to perform other, unrelated functions in addition to those described here. To the extent that a system includes a structure or combination of structures that perform all of the functions recited in a claim, the claim reads on that system, at least with respect to those functions, even if the structures of the system cannot be easily separated into individual devices, each performing exactly the functions of a corresponding device or module recited in the claim. Likewise, a system that includes a processor configured to execute software instructions, in combination with such structures as would be necessary to perform the recited functions, and a memory device in which instructions for the performance of the recited functions are stored, is also within the scope of such a claim.

In operation, the DRI detector 100 is configured to detect conditions that have the potential of provoking DRI and to notify the user, as described, according to one embodiment, below with reference to FIG. 3. Once notified, the user can then take measures to mitigate the danger. A simple response may be for the user to take note of locations where the detector 100 commonly triggers an alert, and thereafter, just prior to passing through such locations, to use an inhaler or mister to moisturize the user's airways prior to inhaling air that may potentially include dangerous pathogens.

According to an embodiment, a mask is provided that includes a mister, which is coupled to automatically release a burst of moist air upon receipt of an alert signal from a device such as the detector 100 of FIG. 2.

Figure 3:
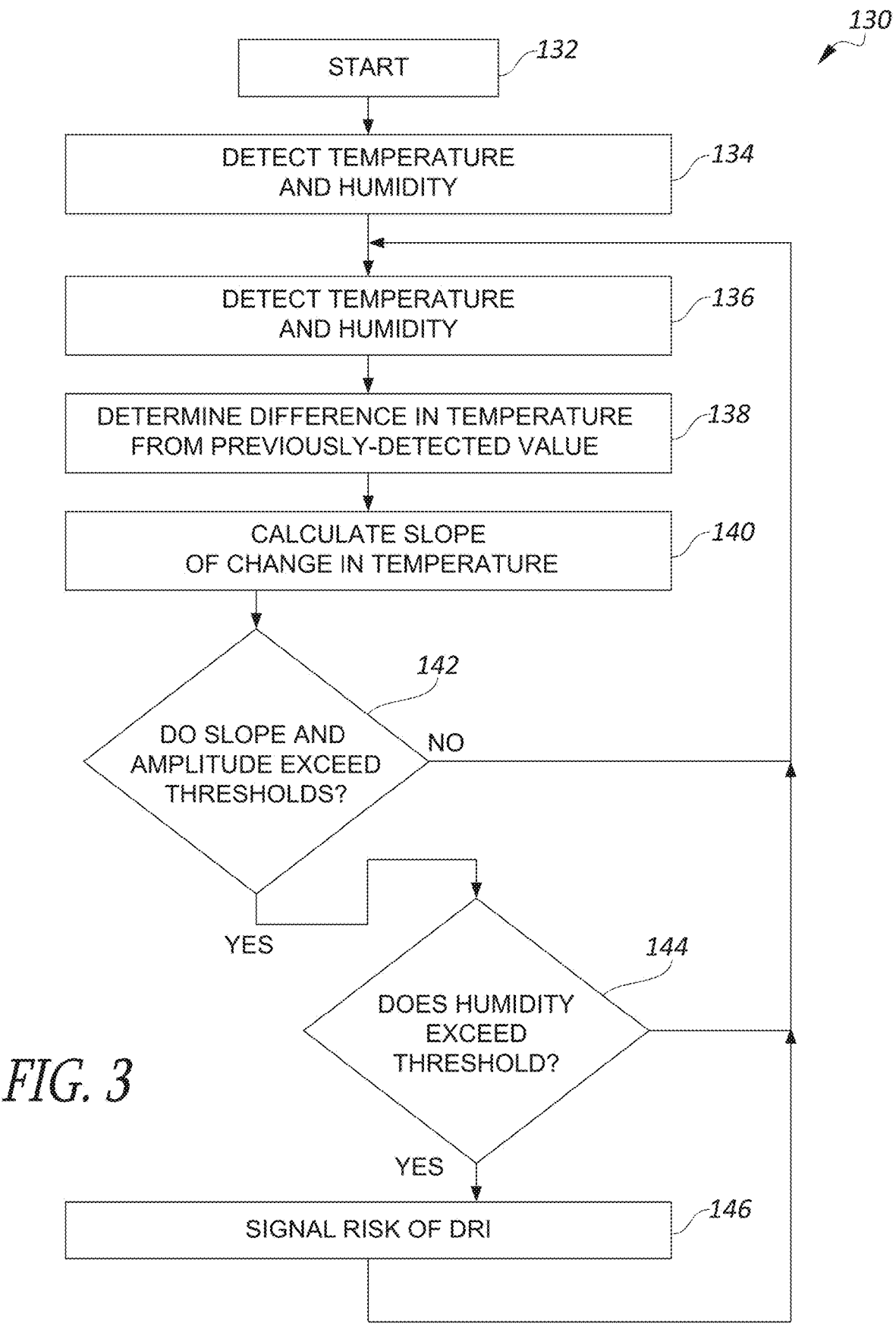

FIG. 3 is a flow chart showing a process 130 for detecting conditions that have the potential of provoking DRI, according to an embodiment. The process 130 can be performed by the DRI detector 100 of FIG. 2, and will be described in that context. However, there are many other types and configurations of devices that can also perform or be configured to perform the process 100. The claims are therefore not limited to the device described above or elsewhere in the present disclosure.

The process 130 is initiated, at step 132, by the user turning the device on or entering a start command, etc. The ambient temperature and humidity are detected and saved in step 134. The temperature and humidity are again detected, in step 136, and saved. According to an embodiment, step 136 is performed a selected time period after performance of step 134, or in the case of a repetition of step 136, the repetition is performed the same selected time period after the previous iteration of the step. According to another embodiment, the detection step 136, and repeats thereof, are performed and the elapsed time between detection steps is also saved.

In step 138, the a previously detected temperature is subtracted from the most recently detected temperature to obtain an amplitude of change. The slope of change is calculated, in step 140. The term amplitude refers to a difference in temperature from one iteration of a detection step 134, 136 to a succeeding iteration. The term slope refers to the degree of change in temperature over the time elapsed between the detection steps in which the change occurred. For example, a change in temperature of ten degrees within a period of two seconds will have a steeper slop than a change of five degrees over the same period.

In step 142, the slope and amplitude are compared with respective thresholds and a determination is made whether the slope and amplitude both exceed respective thresholds. If either value does not exceed its threshold, the process returns to step 136 and repeats from that point. If, however, both thresholds are exceeded, the humidity is compared with a threshold, in step 144, and a determination is made whether the humidity exceeds its threshold. If not, the process again returns to step 136 and repeats from that point. However, if the humidity exceeds its threshold, then in step 146, an alarm signal is sent, indicating that the conditions for potential DRI are present. The process then returns to step 136 and repeats from that point. There are a number of factors that can affect the likelihood of DRI, and therefore may be considered in determining the values of the various thresholds. For example, if the user moves from a warm environment to a cooler environment, but only remains for a short time before moving back to a warm environment, the user's nasal passages will not have dried as much as they would have after a longer period. Thus, according to an embodiment, the slope and/or amplitude thresholds are gradually reduced from initially higher values as the user remains in the cooler environment, so that a greater and/or faster change in temperature is initially required to trigger the alarm signal, but over time the thresholds are reduced. The various detected and calculated values can also influence the thresholds of the other values. For example, if the relative humidity is very high, it would not require as great a change in temperature, or as abrupt, to force precipitation in the nasal passages, and, conversely, if the change in temperature is very great and/or very fast, precipitation will occur even with a much lower relative humidity. Therefore, according to an embodiment, each threshold is configured to vary in response to changes in the other values.

According to another embodiment, only the humidity threshold is adjusted. In the process described with reference to FIG. 3, humidity is compared with its threshold only after the slope and amplitude of the temperature have been determined and compared with their respective thresholds. Therefore, the temperature slope and amplitude thresholds are fixed at a conservative level so that a "YES" value is obtained under any likely conditions. The humidity threshold is then set such that an alarm signal will be produced only if the conditions are actually appropriate.

As noted above, when cold air is warmed, it will become very dry, regardless of its previous degree of humidity. Additionally, most temperate climates include sufficient humidity to reach the dew point with only modest chilling. For example, as can be seen in the chart of FIG. 1, air at a temperature of 95° F. (about 95° C.) with a relative humidity of 50% will reach 100% humidity if chilled to around 75° F. (about 24° C.). Thus, according to a further embodiment, a process is provided in which only the temperature is measured and compared.

According to an embodiment, algorithms are provided for the calculations performed in step 140 and the selection of the thresholds used in steps 142 and 144. According to an alternative embodiment, lookup tables are provided to determine one or more of the temperature slope, and the thresholds for the slope, amplitude, and humidity.

According to an embodiment, a device is provided that is configured to mitigate the danger by providing a clean or sterile humidifying vapor or mist that serves to moisturize the nasal passages without inoculating them with a harmful pathogen. The device is configured to detect the passage of the individual into a CTZ, and respond by outputting a brief flow of vapor during the most vulnerable seconds of transition.

According to another embodiment, a device is provided that is configured to operate in the entrance vestibule of an air conditioned and/or heated building, in which one or more technologies are used to create a safer transition zone between the temperature and humidity extremes of the interior and exterior. This can include maintaining a temperature in the vestibule that is between the higher and lower temperatures, so that a person passing through the vestibule does not experience a single extreme temperature transition, but instead two smaller temperature transitions, neither of which is sufficient to provoke DRI. According to another embodiment, an air curtain is provided within the vestibule that creates a flow of clean humid air to remoisturize the nasal passages and other airways with clean moisture before the individual is exposed to air that may be laden with harmful pathogens.

Figure 4:
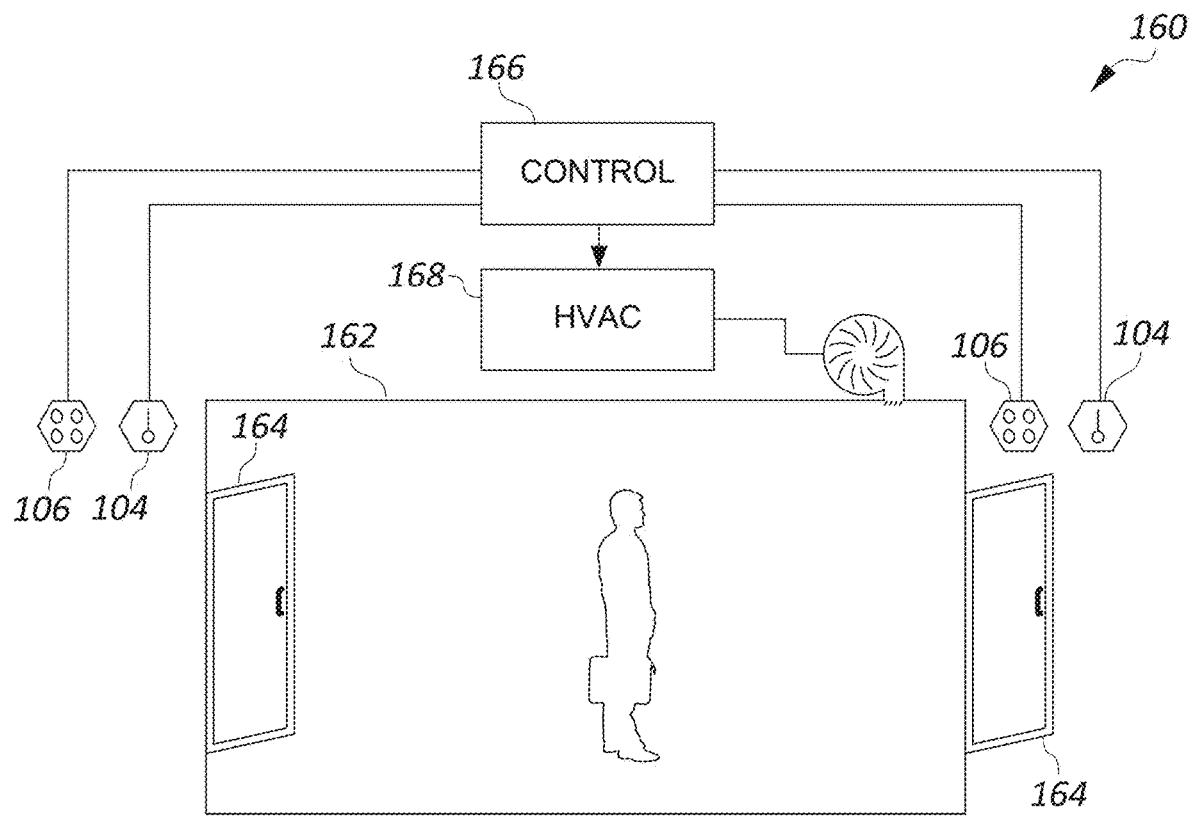

FIG. 4 is a diagrammatic side view showing an example of a system 160 for protecting individuals from DRI as they enter and exit a building, according to an embodiment. The system 160 includes a building vestibule 162 with doors 164 through which individuals pass to enter and exit a building. The system 160 also includes a portion of the building HVAC system 168 that is configured to modify the environment within the vestibule. The controller 166 receives data from temperature and humidity sensors 104, 106 positioned inside and outside the building, and processes the data to detect conditions in which DRI is a potential danger, as described in more detail above. Under such conditions, the controller 166 signals to the HVAC system 168 which regulates the temperature within the vestibule 162 to be between the temperatures inside and outside the building. As people enter and exit the building, and breathe the air in the vestibule, their airways are transitioned more gradually from the extremes of temperature outside the vestibule so that the risk if DRI is reduced or eliminated.

In various of the processes described in the present disclosure, one or more parameters are detected, measured, or determined. As used in the specification and claims, terms such as detect, measure, determine, compare, etc. are not limited to actually obtaining a numerical value for such parameters. For example, the process described with reference to FIG. 3 includes repeated steps of detecting a temperature, at steps 134, 136, obtaining a difference amplitude between the detected temperatures at step 138, and, in step 142, comparing the amplitude with a threshold temperature. While some control systems may be configured to provide actual temperature values, calculate the difference, and then compare the results with a threshold value, there are many alternative solutions that are acceptable; obtaining the actual temperature value, e.g., in degrees Fahrenheit or degrees Celsius, may not be necessary.

For example, according to an embodiment, the temperature sensor is a transducer configured to provide a voltage signal that varies directly or inversely with variations in temperature. A voltage representing a first temperature reading is captured by a first sample and hold (SH) circuit. A voltage representing a second temperature reading is then captured by a second SH circuit and the captured values from the first and second SH circuits is outputted to a differencing circuit, which produces an output voltage that corresponds to the amplitude of a difference between its two inputs. The temperature amplitude threshold is represented by a corresponding reference voltage, and the comparison of the amplitude with the temperature threshold is performed by a comparator circuit coupled to receive the voltage signal from the differencing circuit at a first input and the reference voltage at a second input. The comparator circuit is configured to produce one of two binary values, depending upon which of the two voltage signals is greater, and the resulting binary value indicates whether the amplitude is greater than the threshold, or vice versa.

In the embodiment described above, the numerical values of the actual temperatures are not measured, or determined, in a narrow sense of the term, nor are such values used to calculate the amplitude of change, nor is a numerical value representing the amplitude compared with a numerical value representing the amplitude threshold. Instead, voltage signals that are representative of the actual temperatures are processed to produce another voltage signal that is compared with a voltage signal representative of the threshold value, with the necessary determination being made on the basis of that comparison. Nevertheless, where such a configuration is adequate to make the necessary determination, it is considered to perform the corresponding steps, and would thus fall within the scope of a claim that included a term such as detect, measure, subtract, determine, compare, etc., in referring to such an operation or structure.

Accordingly, claim language referring to or reciting operations involving physical parameters, such as pressure, temperature, humidity, time, rate, power, etc., includes within its scope processes or process steps in which representative or inferred values are manipulated, using, for example, analog or digital circuits, the execution of software instructions, lookup tables, etc., to arrive at a corresponding outcome, even if the actual physical parameters are not employed in the process, and/or are never actually derived.

The abstract of the present disclosure is provided as a brief outline of some of the principles of the invention according to one embodiment, but is not intended as a complete or definitive description of any single embodiment thereof, nor should it be relied upon to define terms used in the specification or claims. The abstract does not limit the scope of the claims.

It will be understood that the scope of the appended claims should not be limited by particular embodiments set forth herein, but should be construed in a manner consistent with the specification as a whole.

What is claimed is:

1. A computer-implemented process for detecting a potential for dewpoint respiratory inoculation (DRI), comprising:
   receiving a signal from a temperature sensor
   detecting a change in temperature over time based on the signal from the temperature sensor;
   determining a slope of change in temperature;
   comparing the slope of change in temperature with a slope threshold stored in a memory module; and
   if the slope of change in temperature exceeds the slope threshold: (i) signaling a potential for dewpoint respiratory inoculation.

2. The computer-implemented process of claim 1, wherein the detecting a change in temperature over time comprises:
   detecting a first temperature based on a first signal from the temperature sensor;
   after detecting the first temperature, detecting a second temperature based on a second signal from the temperature sensor;
   defining a length of time between detecting the first temperature and detecting the second temperature.

3. The computer-implemented process of claim 2, wherein:
   the detecting a second temperature comprises detecting a second temperature after a selected period of time following the detecting a first temperature; and
   the length of time between detecting the first temperature and detecting the second temperature is equal to the selected period of time.

4. The computer-implemented process of claim 2, wherein:
   the defining a length of time between detecting the first temperature and detecting the second temperature comprises measuring an elapsed time between detecting the first temperature and detecting the second temperature.

5. The computer-implemented process of claim 2, comprising:
   selecting the slope threshold based on one of the first or second temperatures.

6. The process of claim 1, wherein the signaling a potential for dewpoint respiratory inoculation comprises producing an audible and/or a visible signal.

7. The process of claim 1, wherein the clean humid air is sterile.

8. The computer-implemented process of claim 1, comprising:
   receiving a signal from a humidity sensor
   determining a relative humidity based on the signal from the humidity sensor;
   comparing the determined relative humidity with a humidity threshold stored in a memory module; and
   wherein the signaling a potential for dewpoint respiratory inoculation includes:
      if the slope of change in temperature exceeds the slope threshold, and if the determined relative humidity exceeds the humidity threshold, then signaling a potential for dewpoint respiratory inoculation.

9. The stored in a memory module process of claim 1, comprising:
   receiving a signal from a humidity sensor;
   determining a relative humidity based on the signal from the humidity sensor; and
   selecting the slope threshold based on the determined relative humidity.

10. A system for detecting a potential for dewpoint respiratory inoculation (DRI), comprising:
    a temperature detection module configured to detect an ambient temperature;
    a clock module; and
    a processor module configured to:
       compare a first temperature detected at a first time with a second temperature detected at second time, after the first time,
       determine a slope of temperature change over time,
       compare the slope of temperature change over time with a slope threshold, and
       signal a potential for DRI if the slope of temperature change over time exceeds the slope threshold.

11. The system of claim 10, comprising:
    a memory module configured to store the first temperature and the first time.

12. The system of claim 10, comprising:
    a humidity detection module configured to detect an ambient humidity.

13. The system of claim 10, comprising a wireless communication module configured to provide communication between a sensor component and a processor component of the system.

14. The system of claim 13, wherein the sensor component includes the temperature detection module and the processor component includes the processor module.

15. The system of claim 14, wherein the processor component is a personal digital device configured to be carried by a user.

16. The system of claim 15, wherein the personal digital device includes a nonvolatile memory containing instructions that are executable by the personal digital device to perform the functions of the processor module.

17. The system of claim 10, further comprising a source of clean humid air.

18. The system of claim 17, wherein the clean humid air is sterile and the source of clean humid air is an inhaler or mister configured release a burst of moist air if the slope of temperature change over time exceeds the slope threshold.

19. A system for detecting a potential for dewpoint respiratory inoculation (DRI) at the entrance or exit of a building, comprising:
    a temperature detection module configured to detect an ambient temperature inside the building and an ambient temperature outside the building;
    a clock module; and
    a processor module configured to:
       compare a first temperature detected inside the building with a second temperature detected outside the building,
       determine a magnitude of temperature change between the first temperature and the second temperature, compare the magnitude of temperature change with a temperature change threshold, and signal a potential for DRI if the magnitude of temperature change exceeds the temperature change threshold.

20. The system of claim 19, further comprising a source of clean humid air, wherein a flow of clean humid air is provided if the magnitude of temperature change exceeds the temperature change threshold.

* * * * *